United States Patent [19]

Sengoku et al.

[11] 4,299,487
[45] Nov. 10, 1981

[54] METHOD OF AND DEVICE FOR ANALYZING ONE INGREDIENT IN A MIXED SOLUTION WITH TWO LIGHT BEAMS OF DIFFERENT WAVELENGTHS

[75] Inventors: Masayuki Sengoku; Tadashi Honkawa; Tadafumi Kuroishi; Ritsuo Komori, all of Katsuta, Japan

[73] Assignee: Hitachi, Ltd., Tokyo, Japan

[21] Appl. No.: 27,099

[22] Filed: Apr. 4, 1979

[30] Foreign Application Priority Data

Apr. 5, 1978 [JP] Japan ................................ 53-39194

[51] Int. Cl.³ .............................................. G01J 3/42
[52] U.S. Cl. ..................................................... 356/320
[58] Field of Search ................ 356/320; 250/343, 344, 250/345, 346

[56] References Cited

U.S. PATENT DOCUMENTS 3,676,005 7/1972 Chance ................................ 356/320
4,136,959 1/1979 Honkawa ............................. 356/320

Primary Examiner—Craig E. Church
Attorney, Agent, or Firm—Craig and Antonelli

[57] ABSTRACT

A method of and device for analyzing one ingredient in a mixed solution with two light beams of different wavelengths are disclosed which include the following processes. A light beam from a light source are divided into a first light beam having a wavelength of $\lambda_1$ and a second light beam having a wavelength of $\lambda_2$. The wavelength $\lambda_1$ is fixed, and $\lambda_2$ is variable, for example, a scanning wavelength. Reference signals $E_{\lambda_1}$ and $E_{(\lambda_2)}$ respectively corresponding to the fixed wavelength $\lambda_1$ and the variable wavelength ($\lambda_2$) are produced from photometric signals resulting from the passage of the first and second light beams through only a solvent. After having been normalized by the reference signals $E_{\lambda_1}$ and $E_{(\lambda_2)}$, the photometric signals $Ib_{\lambda_1}$ and $Ib_{(\lambda_2)}$ resulting from the passage of the first and second light beams through a solution containing only a coexisting ingredient are converted into absorbance signals $b_{\lambda_1}$ and $b_{(\lambda_2)}$. These absorbance signals are held as a ratio indicating signal $k_{(\lambda_2)} = b_{(\lambda_2)}/b_{\lambda_1}$. After having been normalized by the reference signals $E_{\lambda_1}$ and $E_{(\lambda_2)}$, the photometric signals $Ic_{\lambda_1}$ and $Ic_{(\lambda_2)}$ resulting from the passage of the first and second light beams through the mixed solution containing the coexisting ingredient and the ingredient to be analyzed are converted into absorbance signals $C_{\lambda_1}$ and $C_{(\lambda_2)}$. A product signal $k_{(\lambda_2)} \cdot C_{\lambda_1}$ is produced from the absorbance signal $C_{\lambda_1}$ and the ratio indicating signal $k_{(\lambda_2)}$. A signal $\Delta DS = a_{(\lambda_2)} - k_{(\lambda_2)} \cdot a_{\lambda_1}$ which can eliminate the influence of the coexisting ingredient, is produced from the absorbance signal $C_{(\lambda_2)}$ and the product signal $k_{(\lambda_2)} \cdot C_{\lambda_1}$. A signal $\Delta S = a_{(\lambda_2)}/k_{(\lambda_2)} - a_{\lambda_1}$ which indicates the difference-absorbance spectrum of the ingredient to be analyzed, is produced from the signals $\Delta DS$ and $k_{(\lambda_2)}$.

12 Claims, 4 Drawing Figures

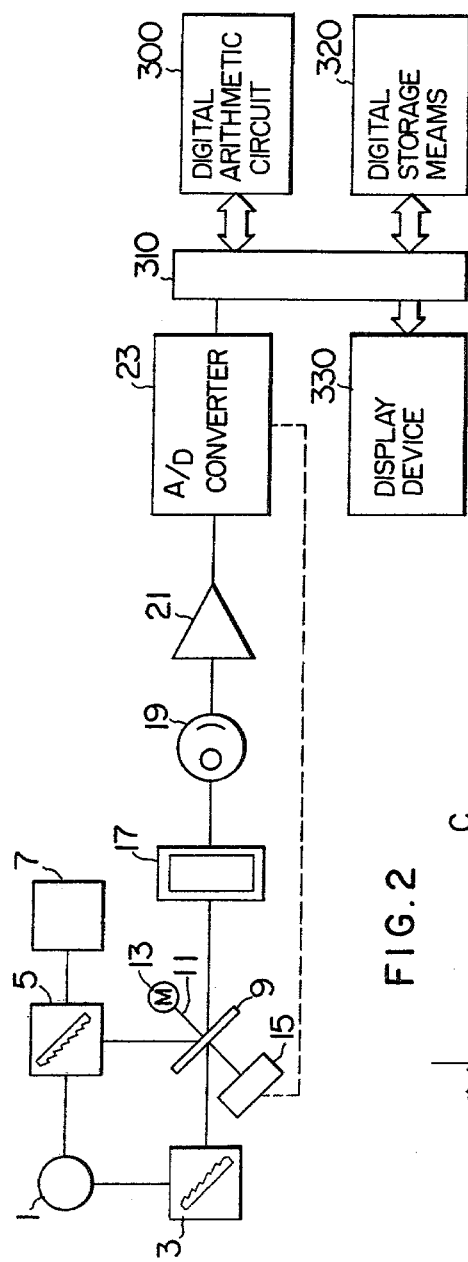
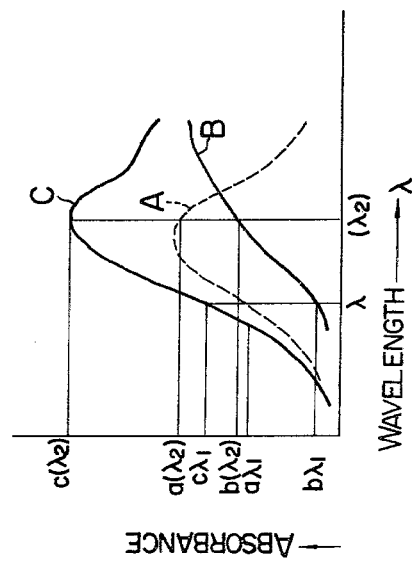
FIG. 4
FIG. 2

METHOD OF AND DEVICE FOR ANALYZING ONE INGREDIENT IN A MIXED SOLUTION WITH TWO LIGHT BEAMS OF DIFFERENT WAVELENGTHS

BACKGROUND OF THE INVENTION

1. FIELD OF THE INVENTION

The present invention relates to a method of and a device for analyzing one ingredient in a mixed solution with two light beams of different wavelengths, and more particularly to an analytical method and instrument suitable for the analysis of an ingredient whose absorption spectrum is unknown in a mixed solution containing more than two kinds of ingredient.

2. DESCRIPTION OF PRIOR ART

The method of and device for analyzing one ingredient in a mixed solution with two light beams of different wavelengths have been proposed in a Japanese Patent Application (Publication No. 44224/77) entitled "Separate and quantitative analysis employing two-wavelength spectrophotometer", and in a Japanese Patent Application (Laid-open No. 91483/77) entitled "Apparatus for analysing one ingredient in a multi-ingredient mixture" which corresponds to a copending U.S. Patent Application Ser. No. 763,674, now U.S. Pat. No. 4,136,959.

The Japanese Patent Application (Publication No. 44224/77) discloses a method of separate and quantitative analysis employing a two-wavelength spectrophotometer such that, in order to determine one ingredient in a mixed solution, any two wavelengths are selected in an absorption spectrum of another ingredient, the wavelengths of the two-wavelength spectrophotometer are set at the selected ones, and an output signal due to another ingredient at one of the set wavelengths is multiplied by a selected factor to be made equal to an output signal due to another ingredient at the other of the set wavelengths, that is, to make a difference absorbance indicated by the spectrophotometer equal to zero, thereby eliminating the disturbance by another ingredient.

The Japanese Patent Application (Laid-open No. 91483/77) teaches an analytical apparatus for directly determining a desired ingredient independently of a coexisting ingredient in which two light beams of different wavelengths pass through a mixture to produce respective photometric signals, the signals are subjected to logarithmic conversion to deliver respective output signals, and the output signals are multiplied by respective factors which make the difference of absorbances due to the coexisting ingredient alone at the two wavelengths equal to zero, to obtain a difference between the output signals thus modified.

The above-mentioned patent applications disclose only a method of and apparatus for determining one ingredient in a mixture containing ingredients, the absorption spectrum of each of which is known, and never teach nor suggest the qualitative analysis or identification of that ingredient contained in a mixture whose absorption spectrum is unknown.

In a medical institution such as a hospital, there is often found such a case that, when a mixture containing ingredients whose absorption spectra are all known is left at rest for a time, the mixture is converted into a different mixture containing an ingredient whose absorption spectrum is unknown. Therefore, it is earnestly required to accomplish a method and apparatus capable of qualitatively indicating what kind of ingredient has been produced with the passage of time. However, an appropriate method and/or apparatus which can satisfy the above-mentioned requirement have not yet been proposed.

Further, it is very difficult to identify or qualitatively determine one ingredient whose absorption spectrum is unknown in a mixture by the method and apparatus described in the above-mentioned Japanese Patent Applications for the following reasons. In order to identify the ingredient having an unknown absorption spectrum, it is necessary to obtain a difference-absorbance spectrum of the ingredient by such a method as fixing one of the measuring wavelengths and varying the other. However, in the method and apparatus according to the Japanese Patent Applications, the factors, by which two photometric signals are multiplied, are so adjusted as to make a difference-absorbance of a coexisting ingredient with respect to two specified wavelengths equal to zero. That is, the optical and electrical conditions are selected and fixed with respect to the specified two wavelengths. Accordingly, it is not possible to scan a sample with the wavelength of light in the abovementioned method and apparatus.

SUMMARY OF THE INVENTION

An object of the present invention is to provide a method of and a device for analyzing one ingredient in a mixed solution with two light beams of different wavelengths which can have a wide range of application.

Another object of the present invention is to provide a method of and a device for qualitatively analyzing one ingredient whose absorption spectrum is unknown, in a mixture.

A further object of the present invention is to provide a method of and a device for quantitatively analyzing at high accuracy one ingredient in a mixture containing plural ingredients, an absorption spectrum of each 2 which is known.

A still further object of the present invention is to provide an analytical method and an analytical instrument, both of which can automatically eliminate any influences of instrumental factors independently of wavelength and have a high operation efficiency.

The principal feature of the present invention is as follows. Photometric signals resulting from the passage of two light beams of different wavelengths through a solvent are employed as reference signals. Photometric signals which result from the passage of the two light beams through a coexisting ingredient and are normalized by the reference signals are employed to produce a signal indicating the ratio of one of the photometric signals concerning the coexisting ingredient to the other. One of the photometric signals, which result from the passage of the two light beams through a mixed solution and are normalized by the reference signals, and the ratio indicating signal are employed to produce a product signal. The product signal and the other of the photometric signals concerning the mixed solution are employed to produce a signal indicating a difference therebetween. The difference indicating signal is produced in the form of a ratio thereof to the ratio indicating signal, as occasion demands. Either one of the two light beams has a plurality of wavelengths.

BRIEF DESCRIPTION OF THE DRAWINGS

FIG. 2 is a graph showing an absorption spectrum of a mixture C which contains an ingredient A whose absorption spectrum is unknown and a coexisting ingredient B whose absorption spectrum is known, and for showing relationships between wavelength and absorbance.

FIGS. 3 and 4 are block diagrams showing different device for analyzing one ingredient in a mixed solution with two light beams of different wavelengths according to other preferred embodiments of the present invention.

DESCRIPTION OF THE PREFERRED EMBODIMENTS

Figure 1:
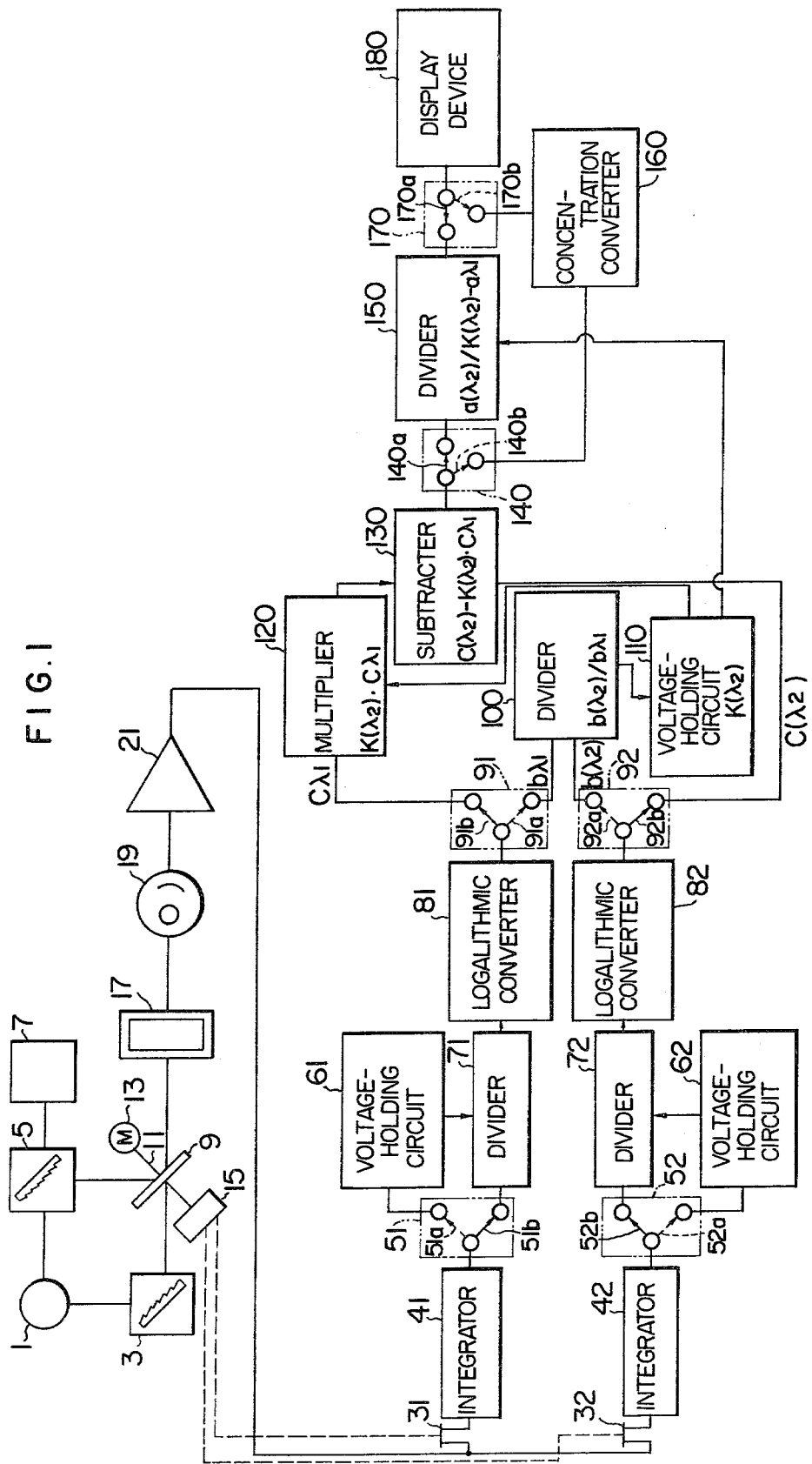
FIG. 1 is a block diagram showing a device for analyzing one ingredient in a mixed solution with two light beams of different wavelengths according to a preferred embodiment of the present invention.

Prior to the explanation of a preferred embodiment of the present invention taken in conjunction with FIG. 1, a principle of the invention, on which a difference-absorbance spectrum is obtained for an ingredient whose absorption spectrum is unknown, is briefly set forth below.

Let us assume that a mixed solution C contains an ingredient A whose absorption spectrum is unknown and a coexisting ingredient B whose absorption spectrum is known. Then, the absorbances at fixed and variable wavelengths $\lambda_1$ and $(\lambda_2)$ are given by the following equations:

$$C_{\lambda_1} = a_{\lambda_1} + b_{\lambda_1} \qquad (1)$$
$$C_{(\lambda_2)} = a_{(\lambda_2)} + b_{(\lambda_2)}$$

where $a_{\lambda_1}$ and $a_{(\lambda_2)}$ indicate absorbances of the ingredient A at wavelengths $\lambda_1$ and $(\lambda_2)$, respectively, $b_{\lambda_1}$ and $b_{(\lambda_2)}$ absorbances of the ingredient B at $\lambda_1$ and $(\lambda_2)$, and $C_{\lambda_1}$ and $C_{(\lambda_2)}$ absorbances of the mixed solution C at $\lambda_1$ and $(\lambda_2)$.

Accordingly, a signal $\Delta DS$ indicating a difference-absorbance spectrum is given by the following equation.

$$\Delta DS = C_{(\lambda_2)} - C_{\lambda_1} \qquad (2)$$
$$= a_{(\lambda_2)} - a_{\lambda_1} + b_{(\lambda_2)} - b_{\lambda_1}$$

Evidently, the signal $\Delta DS$ is affected by the ingredient B. In order to obtain a difference-absorbance spectrum signal $\Delta DS'$ which does not include $b_{\lambda_1}$ and $b_{(\lambda_2)}$, one of absorbances $C_{(\lambda_2)}$ and $C_{\lambda_1}$ of the mixed solution C at wavelengths $(\lambda_2)$ and $\lambda_1$ is multiplied by $k_{(\lambda_2)} = b_{(\lambda_2)}/b_{\lambda_1}$, that is, by a factor which is equal to a ratio of the absorbance $b_{(\lambda_2)}$ of the coexisting ingredient B at the wavelength $(\lambda_2)$ to the absorbance $\lambda_1$ thereof at $\lambda_1$. The desired signal $\Delta DS'$ is given by the following equation;

$$\Delta DS' = C_{(\lambda_2)} - k_{(\lambda_2)} C_{\lambda_1}, \qquad (3)$$
that is, $\Delta DS' = a_{(\lambda_2)} - k_{(\lambda_2)} a_{\lambda_1} + b_{(\lambda_2)} - b_{\lambda_1} b_{(\lambda_2)}/b_{\lambda_1}$
$$= a_{(\lambda_2)} - k_{(\lambda_2)} a_{\lambda_1}. \qquad (4)$$

In the equation 4, since $k_{(\lambda_2)}$ is equal to $b_{(\lambda_2)}/b_{\lambda_1}$, both $a_{(\lambda_2)}$ and $k_{(\lambda_2)} a_{\lambda_1}$ are varied as the wavelength $(\lambda_2)$ is varied. By dividing the right side of the equation 4 by $k_{(\lambda_2)}$, a signal $\Delta S_{(\lambda_2)}$ which is indicated by the following equation is obtained.

$$\Delta S_{(\lambda_2)} = a_{(\lambda_2)}/k_{(\lambda_2)} - a_{\lambda_1} \qquad (5)$$

Evidently, the signal $\Delta S_{(\lambda_2)}$ is a difference signal between a variable signal $a_{(\lambda_2)}/k_{(\lambda_2)}$ which is varied with the variable wavelength $(\lambda_2)$ and a fixed signal $a_{\lambda_1}$, and the equation 5 is a formula of difference-absorbance using the scanning wavelength $(\lambda_2)$ as a parameter. The difference-absorbance spectrum of the ingredient A can be obtained by plotting a difference-absorbance at each wavelength for corresponding wavelength, that is, scanning wavelength.

Though various materials such as a pigment added to foods are actually employed as an ingredient to be identified, the present invention will be explained below with an example in which a mixture C having an absorption spectrum characteristic as shown in FIG. 2 is employed as a test sample, and wherein one ingredient A of the mixture C, whose absorption spectrum is unknown, is qualitatively determined or identified in such a manner as to eliminate the influence of a coexisting ingredient B. Incidentally, in FIG. 2, the abscissa indicates the wavelength, $\lambda_1$ is one fixed wavelength, and $(\lambda_2)$ includes various wavelengths in a range, while the ordinate indicates the absorbance. As can be understood from FIG. 2, the absorbance of the mixture C is equal to the sum of the absorbance of the ingredient A and that of the coexisting ingredient B at each wavelength.

Referring now to FIG. 1, only the solvent of the mixed solution is firstly introduced into a sample cell 17. Then, the working wavelength of an optical grating 3 is fixed at $\lambda_1$ and the working wavelength of an optical grating 5 is varied in a predetermined wavelength range by a wavelength scanning mechanism 7. The variable wavelength or scanning wavelength is represented by $(\lambda_2)$.

Thus, light emitted from a lamp 1 which is employed as a light source is divided into a light beam having the fixed wavelength $\lambda_1$ and a light beam having the scanning or variable wavelength $(\lambda_2)$. The two light beams are alternately incident on the sample cell 17 through a sector-mirror 9 driven by a motor 13. At this time, first and second mode change-over switches 51 and 52 are set at their first modes 51a and 52a, respectively. After having passed the sample cell 17 which contains the solvent alone, the light beam of fixed wavelength $\lambda_1$ and the light beam of variable wavelength $(\lambda_2)$ are alternately detected by a detector 19 to be converted into an electrical signals. The signal are amplified by a pre-amplifier 21, and then are separated into a signal $Is_{\lambda_1}$ resulting from the light beam of fixed wavelength $\lambda_1$ and a signal $Is_{(\lambda_2)}$ resulting from the light beam of variable wavelength $(\lambda_2)$ ($Is_{(\lambda_2)}$ indicates a corresponding signal at each wavelength within a wavelength range), through first and second gates 31 and 32 which are turned on and off by a synchronizing signal from a synchronizing signal generating circuit 15. The synchronizing signal is generated in synchronism with the rotation of the sector-mirror 9. The signals $Is_{\lambda_1}$ and $Is_{(\lambda_2)}$ are integrated in first and second integrators 41 and 42, respectively, to be converted into D.C. signals.

Since the first and second mode change-over switches 51 and 52, as mentioned previously, are set at the first modes 51a and 52a, respectively. The output signals (D.C. signals) from the first and second integrators 41 and 42 are inputted to first and second voltage holding circuits 61 and 62, respectively. The D.C. signals imparted to the first and second holding circuits 61 and 62 are held therein as reference signals $E_{\lambda 1}$ and $E_{(\lambda 2)}$ for respectively correcting instrumental factors of the optical system at both the fixed wavelength $\lambda_1$ and the variable wavelength $(\lambda_2)$. The output signals from the first and second holding circuits 61 and 62 are inputted to first and second dividers 71 and 72. When the first and second mode change-over switches 51 and 52 are respectively changed over to their second modes 51b and 52b in such a condition, the first and second dividers 71 and 72 receive the output signals $Is_{\lambda 1}$ and $Is_{(\lambda 2)}$ from the first and second integrators 41 and 42, respectively, and deliver output signals whose values are both equal to 1. Therefore, first and second logarithmic converters 81 and 82 deliver their output signals whose values are equal to 0. Thus, the zero adjustment for absorbance at each of the wavelengths $\lambda_1$ and $(\lambda_2)$ is automatically conducted. That is, the above circuit construction makes the zero adjustment for absorbance unnecessary, and therefore the analytical procedure is conducted at high operation efficiency and at high accuracy.

As mentioned above, the reference signals $E_{\lambda 1}$ and $E_{(\lambda 2)}$ for automatically eliminating the instrumental factors of the optical system at wavelengths $\lambda_1$ and $(\lambda_2)$ are stored or set in the first and second voltage-holding circuits 61 and 62, respectively.

Next, a solution containing only the coexisting ingredient B whose absorption spectrum is known, is introduced into the sample cell 17 in place of the solvent. In the same manner as the solvent, the light beam of fixed wavelength $\lambda_1$ and the light beam of variable wavelength $(\lambda_2)$ alternately pass through the solution containing the ingredient B alone. At this time, the first and second mode change-over switches 51 and 52 are set at their second modes 51b and 52b.

The light beams which have alternately passed through the solution containing the ingredient B alone, are detected by the detector 19 to be subjected to photoelectric conversion, and an output signal from the detector 19 is amplified by the pre-amplifier 21. An output signal $IB_{\lambda 1}$ resulting from the light beam of wavelength $\lambda_1$ and an output signal $IB_{(\lambda 2)}$ resulting from the light beam of wavelength $(\lambda_2)$ are separated from each other through the first and second gates 31 and 32.

The output signal resulting from the light beam of wavelength $\lambda_1$ is sent through the first gate 31 to the first integrator 41 to be converted into a D.C. signal, and then is inputted to the first divider 71 through the second mode 51b of the first mode changeover switch 51. The output signal $IB_{\lambda 1}$ is divided by the reference signal $E_{\lambda 1}$ in the first divider 71 in order to eliminate the influence of the instrumental factors of the optical system, and an output signal $IB_{\lambda 1}/E_{\lambda 1}$ from the first divider is inputted to the first logarithmic converter 81 to be converted into an absorbance $b_{\lambda 1}$ of the coexisting ingredient B at the wavelength $\lambda_1$.

Similarly, the output signal resulting from the light beam of wavelength $(\lambda_2)$ is sent through the second gate 32 to the second integrator 42 to be converted into a D.C. signal, and then is inputted to the second divider 72 through the second mode 52b of the second mode change-over switch 52. The output signal $IB_{(\lambda 2)}$ is divided by the reference signal $E_{(\lambda 2)}$ in the second divider 72 in order to eliminate the influence of the instrumental factors of the optical system, and an output signal $IB_{(\lambda 2)}/E_{(\lambda 2)}$ from the second divider is inputted to the second logarithmic converter 82 to be converted into an absorbance $b_{(\lambda 2)}$ of the coexisting ingredient B at the variable wavelength $(\lambda_2)$. It is to be noted that the absorbance $b_{(\lambda 2)}$ comprises an absorbance at each wavelength in a predetermined range. At this time, third and fourth mode change-over switches 91 and 92 are set at their first mode 91a and 92a, respectively. The output signal $b_{\lambda 1}$ from the first logarithmic converter 81 and the output signal $b_{(\lambda 2)}$ from the second logarithmic converter 82 are inputted to a third divider 100 through a first mode 91a of a third mode change-over switch 91 and a first mode 92a of a fourth mode change-over switch 92, respectively. The ratio of the output signal $b_{(\lambda 2)}$ to the output signal $b_{\lambda 1}$ is computed in the third divider 100 to deliver an absorbance ratio signal $k_{(\lambda 2)} = b_{(\lambda 2)}/b_{\lambda 1}$. The absorbance ratio signal $k_{(\lambda 2)}$ is held in a third voltage-holding circuit 110 to be inputted to a multiplier 120 and a fourth divider 150 at need.

Next, the mixed solution C containing both the ingredient A whose absorption spectrum is unknown and the coexisting ingredient B is introduced into the sample cell 17 in place of the solution containing the ingredient B alone. In the same manner as the solvent and the solution containing only the ingredient B, the light beam of fixed wavelength $\lambda_1$ and the light beam of variable wavelength $(\lambda_2)$ alternately pass through the mixed solution by means of the sector-mirror 9. At this time, the first and second mode change-over switches 51 and 52 are set at their second modes 51b and 52b, respectively, and the third and fourth mode change-over switches 91 and 92 are set at their second modes 91b and 92b, respectively. Further, fifth and sixth mode change-over switches 140 and 170 are set at their first modes 140a and 170a, respectively.

The light beams which have alternately passed through the mixed solution C are detected by the detector 19 to be subjected to photoelectric conversion, and the electric signal thus obtained are subjected to signal-amplification in the pre-amplifier 21. An output signal $Ic_{\lambda 1}$ resulting from the light beam of wavelength $\lambda_1$ and an output signal $Ic_{(\lambda 2)}$ resulting from the light beam of wavelength $(\lambda_2)$ are separated from each other through the gates 31 and 32 which are turned on and off in synchronism with the rotation of the sector-mirror 9. The output signals $Ic_{\lambda 1}$ and $Ic_{(\lambda 2)}$ are converted into D.C. signals in the integrators 41 and 42, respectively, and then are inputted to the first and second dividers 71 and 72 through the second mode 51b of the first mode change-over siwtch 51 and the second mode 52b of the second mode change-over switch 52, respectively. In these dividers 71 and 72, the output signals $Ic_{\lambda 1}$ and $Ic_{(\lambda 2)}$ are divided by the reference signals $E_{\lambda 1}$ and $E_{(\lambda 2)}$, respectively, in order to eliminate the influence of the instrumental factors of the optical system. An output signal $Ic_{\lambda 1}/E_{\lambda 1}$ from the first divider 71 and an output signal $Ic_{(\lambda 2)}/E_{\lambda 2}$ from the second divider 72 are inputted to the first and second logarithmic converters 81 and 82 to be converted into absorbances $C_{\lambda 1}$ and $C_{(\lambda 2)}$ of the mixed solution at the wavelengths $\lambda_1$ and $(\lambda_2)$, respectively.

The output signal $C_{\lambda 1}$ from the first logarithmic converter 81 is applied to an input terminal of the multiplier 120 through the second mode 91b of the third mode change-over switch 91. At this time, another input terminal of the multiplier 120 receiver the absorbance ratio signal $k_{(\lambda 2)}$ held in the voltage-holding circuit 110. Accordingly, the multiplier 120 delivers an output signal $C_{\lambda 1} \times k_{(\lambda 2)}$ which is applied to an input terminal of a subtracter 130. While, the output signal $C_{(\lambda 2)}$ from the second logarithmic converter 82 is applied to another input terminal of the subtracter 130 through the second mode 92b of the fourth mode change-over switch 92. Thus, the subtraction between the output signal $C_{(\lambda 2)}$ and the output signal $C_{\lambda 1} \times k_{(\lambda 2)}$ is conducted in the subtracter 130. An output signal indicating a difference-absorbance spectrum, that is, $\Delta DS' = C_{(\lambda 2)} - k_{(\lambda 2)} C_{\lambda 1}$ is delivered from the subtracter 130.

Since the mixed solution C contains the ingredient A to be identified and the coexisting ingredient B, the absorbance of the mixed solution C at each of the wavelengths $\lambda_1$ and $(\lambda_2)$, as shown in FIG. 2, is given by the following equations:

$$\begin{cases} C_{\lambda 1} = a_{\lambda 1} + b_{\lambda 1} \\ C_{(\lambda 2)} = a_{(\lambda 2)} + b_{(\lambda 2)}, \end{cases}$$

where $a_{\lambda 1}$ and $a_{(\lambda 2)}$ indicate the absorbance of the ingredient A to be identified at the fixed and variable wavelengths $\lambda_1$ and $(\lambda_2)$, respectively.

Accordingly, the output signal $\Delta DS'$ indicating the difference-absorbance spectrum of the ingredient A to be identified is given by the following equations:

$$\Delta DS' = C_{(\lambda 2)} - k_{(\lambda 2)} C_{\lambda 1}$$
$$= a_{(\lambda 2)} - k_{(\lambda 2)} a_{\lambda 1} + b_{(\lambda 2)} - k_{(\lambda 2)} b_{\lambda 1}$$
$$= a_{(\lambda 2)} - k_{(\lambda 2)} a_{\lambda 1},$$

since $k_{(\lambda 2)} = b_{(\lambda 2)} / b_{\lambda 1}$.

That is, the absorbances $b_{\lambda 1}$ and $b_{(\lambda 2)}$ of the coexisting ingredient B are eliminated from $\Delta DS$.

However, since, in the signal $\Delta DS$ indicating the difference-absorbance spectrum, the absorbance $a_{\lambda 1}$ at the fixed wavelength $\lambda_1$ of the ingredient A to be identified is affected by the absorbance ratio $k_{(\lambda 2)}$ of the coexisting ingredient B, the signal $\Delta DS$ shows spectra of different shapes in dependence on the kind of coexisting ingredient. That is, the signal $\Delta DS$ cannot have a similar shape to the absorption spectrum of the ingredient A. In order to solve this problem, the output signal $\Delta DS$ from the subtracter 130 is inputted to the fourth divider 150 through a first mode 140a of a fifth mode change-over switch 140. In the fourth divider 150, the output signal $\Delta DS$ is divided by the absorbance ratio signal $k_{(\lambda 2)}$ held in the third holding circuit 110. Thus, there can be delivered from the fourth divider 150 an output signal indicating a difference-absorbance spectrum $\Delta S$ which is similar to the absorption spectrum of the ingredient A and is given by the following equation:

$$\Delta S = a_{(\lambda 2)} / k_{(\lambda 2)} - a_{\lambda 1}.$$

The difference-absorbance spectrum $\Delta S$ is sent through a first mode 170a of a sixth mode change-over switch 170 to a display device 180 to be displayed thereat.

As described above, according to one preferred embodiment of the present invention, an ingredient whose absorption spectrum is unknown can be qualitatively analyzed from a mixed solution containing the above ingredient and a coexisting ingredient whose absorption spectrum is known. That is, the present invention has an advantage that various kinds of ingredients can be readily identified.

In the case when a mixed solution contains two kinds of ingredients, the absorption spectrum of each of which is known, the quantitative analysis of a desired ingredient can be conducted in the following manner. The variable wavelength $(\lambda_2)$ is fixed at a specified wavelength $\lambda_2$. Similarly to the above-mentioned procedure, those output signals at the fixed wavelengths $\lambda_1$ and $\lambda_2$ which are concerned with only a solvent, are held as the reference signals in the first and second holding circuits 61 and 62. Next, two kinds of absorbances at the fixed wavelengths $\lambda_1$ and $\lambda_2$ by only the coexisting ingredient B are obtained in the first and second logarithmic converters 81 and 82, respectively. An absorbance ratio signal $k = b_{\lambda 2} / b_{\lambda 1}$ is obtained from the above absorbance signals in the third divider, and is held in the third holding circuit 110.

Next, with the alternate passage of the light beam of wavelength $\lambda_1$ and the light beam of wavelength $\lambda_2$ through the mixed solution, absorbance signals $C_{\lambda 1}$ and $C_{\lambda 2}$ are delivered from the first and second logarithmic converters 81 and 82, respectively. The absorbance signal $C_{\lambda 1}$ from the first logarithmic converter and the absorbance ratio signal k held in the third holding circuit 110 are respectively applied to two inputs of the multiplier 120 to deliver an output signal $kC_{\lambda 1}$. The output signal $kC_{\lambda 1}$ from the multiplier 120 and the output signal $C_{\lambda 2}$ from the second logarithmic converter 82 are both applied to the subtracter 130 to obtain a difference-absorbance signal $DS = C_{\lambda 2} - kC_{\lambda 1}$. Evidently, the following equations hold in this case:

$$\begin{cases} C_{\lambda 1} = a_{\lambda 1} + b_{\lambda 1} \\ C_{\lambda 2} = a_{\lambda 2} + b_{\lambda 2}, \end{cases}$$

where $a_{\lambda 1}$ indicates the absorbance at the wavelength $\lambda_1$ of the ingredient A to be analyzed, and $a_{\lambda 2}$ the absorbance at the wavelength $\lambda_2$.

Accordingly, $$\Delta DS = a_{\lambda 2} - ka_{\lambda 1} + b_{\lambda 2} - kb_{\lambda 1}$$
$$= a_{\lambda 2} - ka_{\lambda 1},$$

since $$k = b_{\lambda 2} / b_{\lambda 1}.$$

Since the absorbance ratio signal k is given by the ratio of the absorbance at the fixed wavelength $\lambda_2$ of the coexisting ingredient B to that at the fixed wavelength $\lambda_1$, the signal is considered constant. Thus, $\Delta DS$ can indicate the difference-absorbance of the ingredient A without suffering from the influence of the coexisting ingredient B.

The difference-absorbance signal $\Delta DS$ obtained as above is applied to a concentration converter 160 through a second mode 140b of the fifth mode change-over switch 140 to be converted to a concentration signal. The concentration signal is inputted to the display device 180 through a second mode 170b of the sixth mode change-over switch 170 to directly display the concentration of the ingredient A.

As mentioned above, only by setting the working wavelength of the optical grating 5 at a fixed wavelength, it is possible to quantitatively analyze one ingredient in a mixed solution containing two ingredients, the absorption spectrum of each of which is known, and to directly indicate the result of analysis in the form of concentration.

In the above-mentioned embodiment of the present invention, the first, second, third, fourth, fifth and sixth mode change-over switches 51, 52, 91, 92, 140 and 170 are changed over to their first or second modes whenever the solvent, the solution containing the coexisting ingredient B alone, or the mixed solution C is introduced into the sample cell 17. However, it is possible to automatically change over these switches in synchronism with the replacement of sample in the sample cell 17 by combining a cell programmer and so on with the construction shown in FIG. 1.

Figure 3:
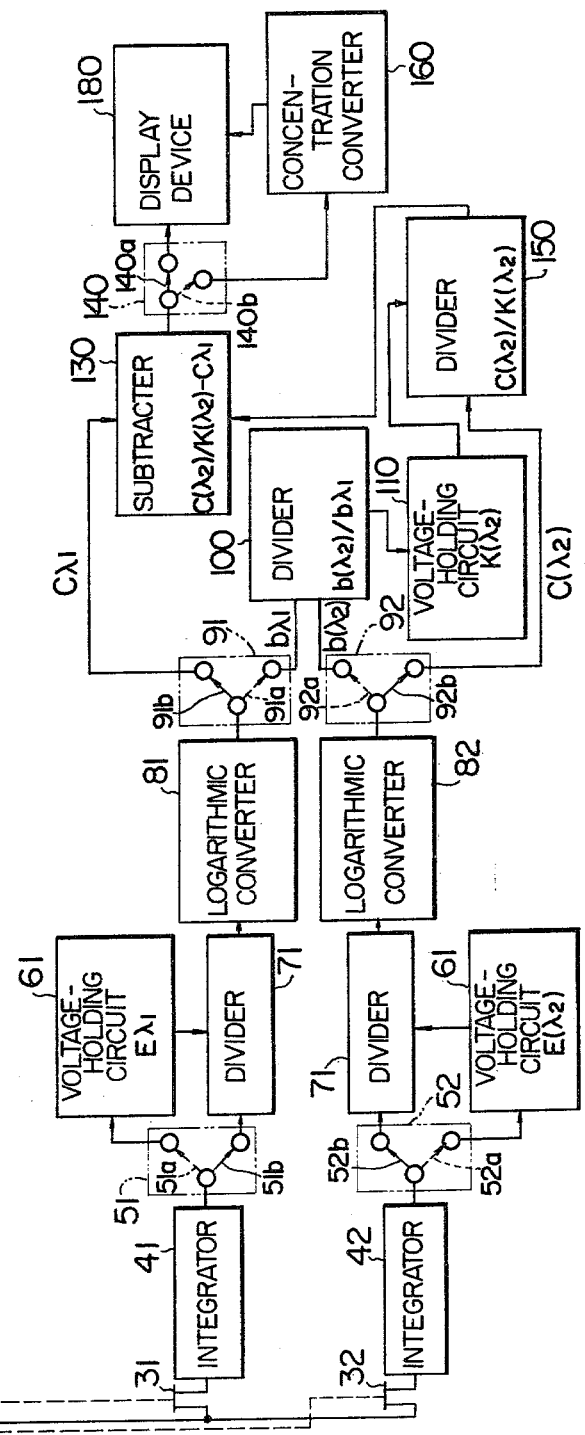

FIG. 3 is a block diagram of a device for analyzing one ingredient in a mixed solution with two light beams of different wavelengths according to another embodiment of the present invention. Like parts in FIGS. 1 and 2 are indicated by like reference numerals.

The construction shown in FIG. 3 is different from that shown in FIG. 1 in the following points. Referring to FIG. 3, an absorbance signal $C_{(\lambda_2)}$ resulting from a light beam of variable wavelength $(\lambda_2)$, which has passed through a mixed solution, and an absorbance ratio signal $k_{(\lambda_2)} = b_{(\lambda_2)}/b_{\lambda_1}$ hold in a voltage-holding circuit 110 are both applied to a divider 150 to produce a ratio signal $C_{(\lambda_2)}/k_{(\lambda_2)}$. The ratio signal $C_{(\lambda_2)}/k_{(\lambda_2)}$ and an absorbance signal $C_{\lambda_1}$ resulting from a light beam of fixed wavelength $\lambda_1$ which has passed through the mixed solution, are both applied to a subtracter 130 to obtain an output signal indicating a difference-absorbance spectrum $\Delta S = C_{(\lambda_2)}/k_{(\lambda_2)} - C_{\lambda_1}$. It is evident from the following equations that the output signal $\Delta S$ from the subtracter 130 indicates the differenceabsorbance spectrum of the ingredient A without suffering from the influence of the coexisting ingredient B:

$$\Delta S = C_{(\lambda_2)}/k_{(\lambda_2)} - C_{\lambda_1}$$
$$= (a_{(\lambda_2)} + b_{(\lambda_2)})/k_{(\lambda_2)} - (a_{\lambda_1} + b_{\lambda_1})$$
$$= a_{(\lambda_2)}/k_{(\lambda_2)} - a_{\lambda_1},$$

since $$k_{(\lambda_2)} b_{(\lambda_2)}/b_{\lambda_1}.$$

Further, it is possible to analyze quantitatively an ingredient whose absorption spectrum is known, by fixing the variable wavelength $(\lambda_2)$ at a specified wavelength $\lambda_2$ in the construction shown in FIG. 3.

The embodiment shown in FIG. 3 has an advantage that it is simple in circuit arrangement as compared with the embodiment shown in FIG. 1.

In the above-mentioned embodiments of the present invention, such electrical elements as arithmetic elements and voltage-holding circuits are all of analog type. However, a device according to the present invention can be constructed employing a digital arithmetic circuit including a central processing unit (CPU) and a digital storage means, as shown in FIG. 4.

Referring to FIG. 4, a digital arithmetic circuit 300 has such a function as performing various kinds of operations which are conducted in the dividers, logarithmic converters, multipliers and subtracters shown in FIGS. 1 and 3, and is connected to an A/D converter 23 through a bus line 310. The A/D converter 23 sends alternately a digital signal resulting from a light beam of a fixed wavelength $\lambda_1$ and a digital signal resulting from a light beam of a variable wavelength $(\lambda_2)$ (or a fixed wavelength $\lambda_2$) to the arithmetic circuit 300 through the bus line 310 in synchronism with the rotation of a sector-mirror 9. The arithmetic circuit 300 is further connected to a digital storage means 320 through the bus line 310. The digital storage means 320 performs the function of the voltage-holding circuits shown in FIGS. 1 and 3 in a digital fashion. The result of operation conducted in the arithmetic circuit 300 is sent through the bus line 310 to the digital storage means 320 to be stored therein, or sent to a display device 330 to be displayed in an analog or digital fashion. The analytical procedure explained in conjunction with FIGS. 1 and 3 is memorized in the digital storage means 320, and the necessary operation is performed in accordance with the memorized procedure.

An electric signal resulting from a light beam of a fixed wavelength $\lambda_1$ which has passed a solvent and an electric signal resulting from a light beam of a variable wavelength $(\lambda_2)$ which has also passed through the solvent, are converted by the A/D converter 23 into digital signals, and then are sent to the digital arithmetic circuit 300 through the bus line 310. In the circuit 300, reference signals are produced which make the absorbance of solvent at each of the wavelengths $\lambda_1$ and $(\lambda_2)$ equal to zero. These reference signals are sent through the bus line 310 to the digital storage means 320, and are stored therein.

Next, an electric signal resulting from a light beam of the fixed wavelength $\lambda_1$ which has passed through a solution containing a coexisting ingredient alone and an electric signal resulting from a light beam of the variable wavelength $(\lambda_2)$ which has passed through the above solution, are respectively converted by the A/D converter 23 into digital signals, and then are sent to the digital arithmetic circuit 300 through the bus line 310. The digital signals which have been sent to the circuit 300 are respectively divided by the reference signals which are read out of the digital storage means 320 through the bus line 310. Then, the ratio of one of the digital signals thus modified to the other is computed in the digital arithmetic circuit 300, and is sent through the bus line 310 to the digital storage means 320 to be stored therein.

Subsequently, an electric signal resulting from a light beam of the fixed frequency $\lambda_1$ which has passed through a mixed solution and an electric signal resulting from a light beam of the variable wavelength $(\lambda_2)$ which has passed through the mixed solution, are respectively converted by the A/D converter 23 into digital signals to be sent to the digital arithmetic circuit 300 through the bus line 310. The following operation is performed in the digital arithmetic circuit 300. That is, the digital signals are respectively normalized by the corresponding reference signals. The normalized digital signal resulting from the light beam of the fixed wavelength $\lambda_1$ is multiplied by the ratio signal which is read out of the storage means 320 through the bus line 310, to produce a product signal. The product signal is subtracted from the normalized digital signal resulting from the light beam of the variable wavelength $(\lambda_2)$, to produce a difference signal. The difference signal is divided by the ratio signal to produce a difference-absorbance signal. The difference-absorbance signal thus obtained is applied to the display device 330 through the bus line 310, to display a difference absorbance spectrum of the desired ingredient.

In a case that a difference-absorbance of an ingredient whose absorption spectrum is known is required, the above-mentioned variable wavelength ($\lambda_2$) is fixed at a specified wavelength $\lambda_2$, and a similar procedure is conducted. However, in this case, there is no necessity for dividing the difference signal by the ratio signal. That is, the difference signal is applied to the display device 330 to display the difference-absorbance or concentration of the ingredient. that a high-precision and rapid analysis can be achieved by employing a digital operation system in place of an analog operation system.

It is needless to say that, with respect to the optical system from the light source down to the detector, the present invention is applicable for devices including other optical systems than that shown in FIG. 1. For example, it is possible to employ a multi-wavelength spectrophotometer after a light beam from a light source has directly passed through a sample cell.

As described above, according to the present invention, a device can be constructed in an analog or digital fashion, and the qualitative and quantative analysis can be conducted while eliminating automatically the influence of the instrumental factors of the optical system. Therefore, the present invention can enjoy such advantages that the analytical method and device are of wide application, and that a high-precision and rapid analysis is conducted.

We claim:

1. A method of analyzing one ingredient in a mixed solution with two light beams of different wavelengths comprising:
   a first step of passing a first light beam having a wavelength fixed at a predetermined value and a second light beam which is scanned over a range of wavelengths, selectively through a solvent to obtain first and second photometric signals corresponding to said first and second light beams passed through said solvent, respectively;
   a second step of producing first and second reference signals from said first and second photometric signals, respectively;
   a third step of passing said first and second light beams through a first solution containing only a first ingredient in said solvent to obtain third and fourth photometric signals corresponding to said first and second light beams passed through said first solution respectively, said first ingredient being one of the ingredients contained in said mixed solution;
   a fourth step of obtaining a first normalized signal by normalizing said third photometric signal by said first reference signal and a second normalized signal by normalizing said fourth photometric signal by said second reference signal;
   a fifth step of producing a signal indicating a ratio of said second normalized signal to said first normalized signal;
   a sixth step of passing said first and second light beams through said mixed solution to obtain fifth and sixth photometric signals corresponding to said first and second light beams passed through said mixed solution, respectively;
   a seventh step of obtaining a third normalized signal by normalizing said fifth photometric signal by said first reference signal and a fourth normalized signal by normalizing said sixth photometric signal by said second reference signal;
   an eighth step of producing a signal indicating a product of said third normalized signal and the ratio indicating signal produced in the fifth step; and
   a ninth step of producing a signal indicating a difference between said signal produced in the eighth step and said fourth normalized signal.

2. A method according to claim 1 further comprising a tenth step of producing a signal indicating a ratio of the difference indicating signal produced in said ninth step to the ratio indicating signal produced in said fifth step.

3. A method of analyzing one ingredient in a mixed solution with two light beams of different wavelengths comprising:
   a first step of passing a first light beam having a wavelength fixed at a predetermined value and a second light beam which is scanned over a range of wavelengths, selectively through a solvent to obtain first and second photometric signals corresponding to said first and second light beams passed through said solvent, respectively;
   a second step of producing first and second reference signals from said first and second photometric signals, respectively;
   a third step of passing said first and second light beams through a first solution containing only a first ingredient in said solvent to obtain third and fourth photometric signals corresponding to said first and second light beams passed through said first solution respectively, said first ingredient being one of the ingredients contained in said mixed solution;
   a fourth step of obtaining a first normalized signal by normalizing said third photometric signal by said first reference signal and a second normalized signal by normalizing said fourth photometric signal by said second reference signal;
   a fifth step of producing a signal indicating a ratio of said second normalized signal to said first normalized signal;
   a sixth step of passing said first and second light beams through said mixed solution to obtain fifth and sixth photometric signals corresponding to said first and second light beams passed through said mixed solution, respectively;
   a seventh step of obtaining a third normalized signal by normalizing said fifth photometric signal by said first reference signal and a fourth normalized signal by normalizing said sixth photometric signal by said second reference signal;
   an eighth step of producing a signal indicating a ratio of said fourth normalized signal and said ratio indicating signal produced in the fifth step; and
   a ninth step of producing a difference indicating signal indicating a difference between the ratio signal produced in said eighth step and said third normalized signal.

4. A method according to claim 3, wherein said first and second reference signals are produced in said second step so that absorbances corresponding to said first and second photometric signals resulting from said first and second light beams having passed through said solvent are substantially equal to zero at the respective wavelengths of the second light beam.

5. A method according to claim 1 or 2, wherein said first and second reference signals are produced in said second step to that absorbances corresponding to said first and second photometric signals resulting from said first and second light beams having passed through said solvent are substantially equal to zero at the respective wavelengths of the second light beam.

6. A device for analyzing one ingredient in a mixed solution with two light beams of different wavelengths comprising:

first means for passing a first light beam having a wavelength fixed at a predetermined value and a second light beam which is scanned over a range of wavelengths through a mixed solution containing a first ingredient the absorbance spectrum of which is known and at least one additional ingredient to be analyzed to obtain first and second photometric signals corresponding to the first and second light beams;

second means for producing a ratio indicating signal indicating a ratio of a fourth photometric signal obtained by passing said second light beam through a first solution containing only the first ingredient to a third photometric signal obtained by passing said first light beam through said first solution;

third means for producing a further signal indicating the product of said first photometric signal and said ratio indicating signal; and fourth means for producing a difference indicating signal indicating a difference between said second photometric signal and said further signal.

7. A device according to claim 6 wherein said second means includes means for holding photometric signals resulting from said first and second light beams having passed through a solvent as reference signals respectively, and means for producing a signal indicating a ratio of each of said first and second photometric signals resulting from said first and second light beams having passed through said mixed solution to a corresponding one of said reference signals.

8. A device according to claim 6 further comprising fifth means for producing a signal indicating the ratio of the difference indicating signal produced in said fourth means to the ratio indicating signal produced in said second means.

9. A method of analyzing one ingredient in a mixed solution with two light beams of different wavelengths comprising:

a first step of passing a first light beam having a wavelength fixed at a predetermined value and a second light beam which is scanned over a range of wavelengths through a mixed solution containing a first ingredient, the absorbance spectrum of which is known, to obtain first and second photometric signals corresponding to the first and second light beams passed through the mixed solution, respectively;

a second step of producing a ratio indicating signal indicating a ratio of a fourth photometric signal obtained by passing said second light beam through a second solution containing only the first ingredient to a third photometric signal obtained by passing said first light beam through said second solution;

a third step of producing a further signal indicating the product of said first photometric signal and said ratio indicating signal; and a fourth step of producing a difference indicating signal indicating a difference between said second photometric signal and said further signal derived from said first photometric signal and said ratio indicating signal.

10. A method according to claim 9 further comprising a fifth step of producing a signal indicating a ratio of the difference indicating signal produced in said fourth step to the ratio indicating signal produced in said second step.

11. A device for analyzing one ingredient in a mixed solution with two light beams of different wavelengths comprising:

a first means for passing a first light beam having a wavelength fixed at a predetermined value and a second light beam which is scanned over a range of wavelengths selectively through a solvent to obtain first and second photometric signals corresponding to the first and second light beams passed through the solvent, respectively;

a second means for producing first and second reference signals from the first and second photometric signals respectively;

a third means for producing third and fourth photometric signals by passing the first and second light beams through a solution containing only a first ingredient, the absorbance spectrum of which is known, instead of the solvent;

a fourth means for producing a first normalized signal by normalizing the third photometric signal by the first reference signal and a second normalized signal by normalizing the fourth photometric signal by the second reference signal;

a fifth means for producing a signal indicating a ratio of the second normalized signal to the first normalized signal;

a sixth means for storing the first and second reference signals and the ratio indicating signal;

a seventh means for producing fifth and sixth photometric signals by passing the first and second light beams through the mixed solution containing the first ingredient and ingredient to be analyzed, instead of the solution, an eighth means for producing a third normalized signal by normalizing the fifth photometric signal by the first reference signal and a fourth normalized signal by normalizing the sixth photometric signal by the second reference signal;

a ninth means for producing a signal indicating a product of the third normalized signal and the ratio indicating signal produced in said fifth means; and a tenth means for producing a signal indicating a difference between the signal produced in said ninth means and the fourth normalized signal.

12. A device according to claim 11 further comprising an eleventh means for producing a signal indicating a ratio of the difference indicating signal produced in said tenth means to the ratio indicating signal produced in said fifth means.

* * * * *